United States Patent
Jeong

(10) Patent No.: US 10,025,898 B2
(45) Date of Patent: Jul. 17, 2018

(54) GRAPHIC USER INTERFACE FOR A THREE DIMENSIONAL BOARD INSPECTION APPARATUS

(71) Applicant: KOH YOUNG TECHNOLOGY INC., Seoul (KR)

(72) Inventor: Joongki Jeong, Gwangmyeong-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 72 days.

(21) Appl. No.: 14/916,361

(22) PCT Filed: Sep. 3, 2014

(86) PCT No.: PCT/KR2014/008220
§ 371 (c)(1),
(2) Date: Mar. 3, 2016

(87) PCT Pub. No.: WO2015/034244
PCT Pub. Date: Mar. 12, 2015

(65) Prior Publication Data
US 2016/0224718 A1    Aug. 4, 2016

(30) Foreign Application Priority Data

Sep. 3, 2013    (KR) .................. 10-2013-0105389

(51) Int. Cl.
*G06F 17/50*    (2006.01)
*G06F 3/0484*   (2013.01)
(Continued)

(52) U.S. Cl.
CPC ....... *G06F 17/5081* (2013.01); *G01R 31/309* (2013.01); *G06F 3/0484* (2013.01);
(Continued)

(58) Field of Classification Search
CPC ........ G01N 2021/95638; G01R 31/309; G06F 17/5081; G06F 3/04815; G06F 3/0484
See application file for complete search history.

(56) References Cited

U.S. PATENT DOCUMENTS 6,434,264 B1    8/2002  Asar
6,825,856 B1 *  11/2004 Fazzio ................. G05B 19/401
                                                         345/646
2010/0246931 A1  9/2010  Kim et al.

FOREIGN PATENT DOCUMENTS

JP    2003-279333    10/2003
JP    2006-208237    8/2006
(Continued)

OTHER PUBLICATIONS

International Search Report for International Application No. PCT/KR2014/008220, dated Nov. 27, 2014.
(Continued)

*Primary Examiner* — Vuthe Siek
(74) *Attorney, Agent, or Firm* — Kile Park Reed & Houtteman PLLC

(57) ABSTRACT

The present invention relates to a graphic user interface for a 3D board inspection apparatus. The graphic user interface includes an actual measurement image display area in which a 3D actual measurement image of an inspection target is displayed based on 3D actual measurement data for the inspection target on a board, and a dimension setup display area in which a dimension of the inspection target in CAD data, a dimension of the inspection target in the 3D actual measurement data and a recommend dimension of the inspection target based on the 3D actual measurement data are displayed. A first contour line of the inspection target based on the dimension of the inspection target in the CAD data and a second contour line of the inspection target based on the 3D actual measurement data is displayed with over- (Continued)

lapping the 3D actual measurement image of the inspection target in the actual measurement image display area.

20 Claims, 2 Drawing Sheets

(51) Int. Cl.
  *G06F 3/0481* (2013.01)
  *G01R 31/309* (2006.01)
  *G01N 21/956* (2006.01)
(52) U.S. Cl.
  CPC .................. *G06F 3/04815* (2013.01); *G01N 2021/95638* (2013.01)

(56) References Cited

FOREIGN PATENT DOCUMENTS

| | | |
|---|---|---|
| JP | 2007-299167 | 11/2007 |
| JP | 2010-244406 | 10/2010 |
| KR | 10-2011-0089519 | 8/2011 |
| WO | 01/20310 | 3/2001 |

OTHER PUBLICATIONS

A Complete Front and Back End Test Solution—Agilent Medalist Automated Optical Inspection; pp. 1-10; Feb. 10, 2007; retrieved from the Internet URL:http://cp.literature.agilent.com/litweb/pdf/5989-6163EN.pdf (retrieved on Mar. 22, 2017).

\* cited by examiner

GRAPHIC USER INTERFACE FOR A THREE DIMENSIONAL BOARD INSPECTION APPARATUS

TECHNICAL FIELD

The present invention relates to a graphic user interface for a three dimensional board inspection apparatus, and more particularly a graphic user interface for a three dimensional board inspection apparatus displaying a component contour line based on a component dimension in reference dimension information that is previously stored in a 3D board inspection apparatus and a component contour line obtained based on actual measurement data with overlapping each other, and displaying recommended dimension information, to easily update reference dimension information by a user.

BACKGROUND ART

Recently, a printed circuit board (PCB) is being minimized so as to mount a high-integrated component thereon thanks to progress of electronic technology, which becomes more and more important as a fundamental factor to increase degree of integration of the PCB.

In order to secure quality of the PCB, an automated optical inspector (AOI) as an apparatus that inspects mounting defects by using a vision function is necessary equipment, and performs inspection based on a predetermined program. The AOI inspects whether leads of a component is attached to a PCB well or not by using 3D image data.

The AOI includes a display to monitor an inspection result, and a user-oriented graphic user interface is required so that a user easily checks the inspection result by the display, and conveniently sets up an inspection condition.

DISCLOSURE

Technical Problem

In order to solve the technical problem, the present invention provides a graphic user interface for a 3D board inspection apparatus displaying a contour line according to reference dimension information that is previously stored and a contour line according to actual measurement with overlapping each other in a 3D actual measurement image of an inspection target, and easily updating reference dimension information with recommended dimension by a user.

The object of the present invention is not limited to the above, and another objects not described above can be clearly understood from the following description by those skilled in the art belonging to the present invention.

Technical Solution

In an exemplary embodiment of the present invention, a graphic user interface for a three dimensional (3D) board inspection apparatus includes an actual measurement image display area in which a 3D actual measurement image of an inspection target is displayed based on 3D actual measurement data for the inspection target on a board, and a dimension information display area in which dimension information of the inspection target is displayed based on the 3D actual measurement data for the inspection target and reference dimension information of the inspection target previously stored in the board inspection apparatus. A first contour line of the inspection target based on the reference dimension information and a second contour line of the inspection target based on the 3D actual measurement data is displayed with overlapping the 3D actual measurement image of the inspection target in the actual measurement image display area.

The dimension information display area may include a reference dimension display area for displaying the reference dimension information, an actual measurement dimension display area for displaying the 3D actual measurement data and a recommended dimension display area for displaying recommended dimension information of the inspection target.

A setup menu is displayed in the dimension information display area for updating the reference dimension information with the recommended dimension information of the inspection target that is previously stored.

Update for the reference dimension information of the inspection target that is previously stored replaced with the recommended dimension information corresponding to the one of width, length and height may be automatically performed when a specific input is input at one location of width, length and height of the first contour line or the second contour line.

In the dimension information display area, a setup menu for update for the reference dimension information replaced with the recommended dimension information of the inspection target that is previously stored may be displayed.

The inspection target may be a component mounted on the board or a lead of the component.

The first contour line and the second contour line may include at least one of a width line, a length line and a height line of the inspection target.

The first contour line and the second contour line may be displayed in a different color from each other.

In case that a ratio of a dimension of the inspection target in the 3D actual measurement data to a dimension of a component corresponding to the inspection target in CAD data deviates from a predetermined range, a recommended dimension may be displayed distinguishable in the dimension setup display area.

The 3D actual measurement image of the inspection target may be displayed rotatable with respect to one of X-axis, Y-axis and Z-axis according to an input value in the actual measurement image display area.

The graphic user interface for a 3D board inspection apparatus may include a reference value setup menu, and when the reference value setup menu is selected, the dimension information display area may be displayed in a pop-up window form.

When a pointer is located on the first contour line or the second contour line, at least one of width, length and height of the inspection target may be displayed at the location.

A program including commands for implementing the graphic user interface for a 3D board inspection apparatus may be stored in a recording medium.

Advantageous Effects

According to a graphic user interface for a 3D board inspection apparatus in an exemplary embodiment of the present invention, a user may easily check a difference between a dimension in CAD data and a dimension in actual measurement on 3D actual measurement image of a component, and further easily update reference dimension information previously stored in a 3D board inspection apparatus with a recommended dimension, to thereby increase user's convenience.

The advantageous effects of the present invention are not limited to the above, and another effects not described above can be clearly understood from the following description by those skilled in the art belonging to the present invention.

MODE FOR INVENTION

Figure 1:
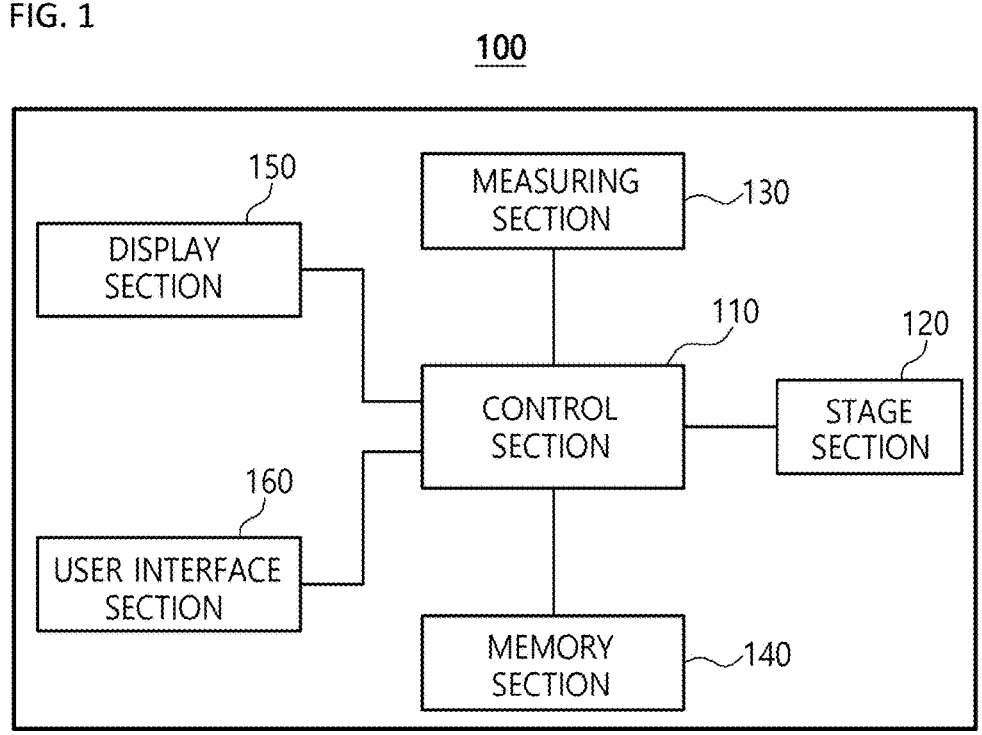
FIG. 1 is a block diagram illustrating a 3D board inspection apparatus for providing a graphic user interface according to an exemplary embodiment of the present invention.

The objects, the effects and the technical features of the present invention for obtaining them will be clearer with reference to the accompanying embodiments and drawings. In explaining the present invention, explanation of well-known function or structure, etc. that may get out of the point will be omitted. The terminology used herein is defined in consideration of a structure, a role, a function, etc. and may be changed according to an intention of a user or a practice.

However, the present invention may be embodied in many different forms and should not be construed as limited to the example embodiments set forth herein. Rather, these example embodiments are provided so that this disclosure will be thorough and complete, and will fully convey the scope of the present invention to those skilled in the art, and the present invention should be limited by claims. Therefore, the definition should be understood throughout the specification.

The objects, the effects and the technical features of the present invention for obtaining them will be clearer with reference to the accompanying embodiments and drawings. In explaining the present invention, explanation of well-known function or structure, etc. that may get out of the point will be omitted. The terminology used herein is defined in consideration of a structure, a role, a function, etc. and may be changed according to an intention of a user or a practice.

However, the present invention may be embodied in many different forms and should not be construed as limited to the example embodiments set forth herein. Rather, these example embodiments are provided so that this disclosure will be thorough and complete, and will fully convey the scope of the present invention to those skilled in the art, and the present invention should be limited by claims. Therefore, the definition should be understood throughout the specification.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, the terms "unit", "section", etc. indicates a unit performing at least one function or operation, and may be realized by a hardware, a software or combination of a hardware and a software.

In addition, each block of the attached block diagram and each step of the attached flow chart and/or combination thereof may be performed by instructions of a computer program. The instructions of a computer program may be installed in a processor of a general computer, a specific computer or a programmable data-processing device. Further, instructions implemented by a processor of a computer or a programmable data-processing device form a means for performing functions described in each block of a block diagram or each step of flow chart.

In addition, each block or each step may represent a part of a module, a segment or a code, which include one or more feasible instructions for implementing specific logical function(s). For example, continuously shown two blocks or steps, in fact, may be simultaneously performed or sometimes reversibly performed according to the function thereof.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, with reference to the drawings, preferred embodiments of the present invention will be described in detail.

Hereinafter, with reference to the drawings, preferred embodiments of the present invention will be described in detail.

Figure 2:
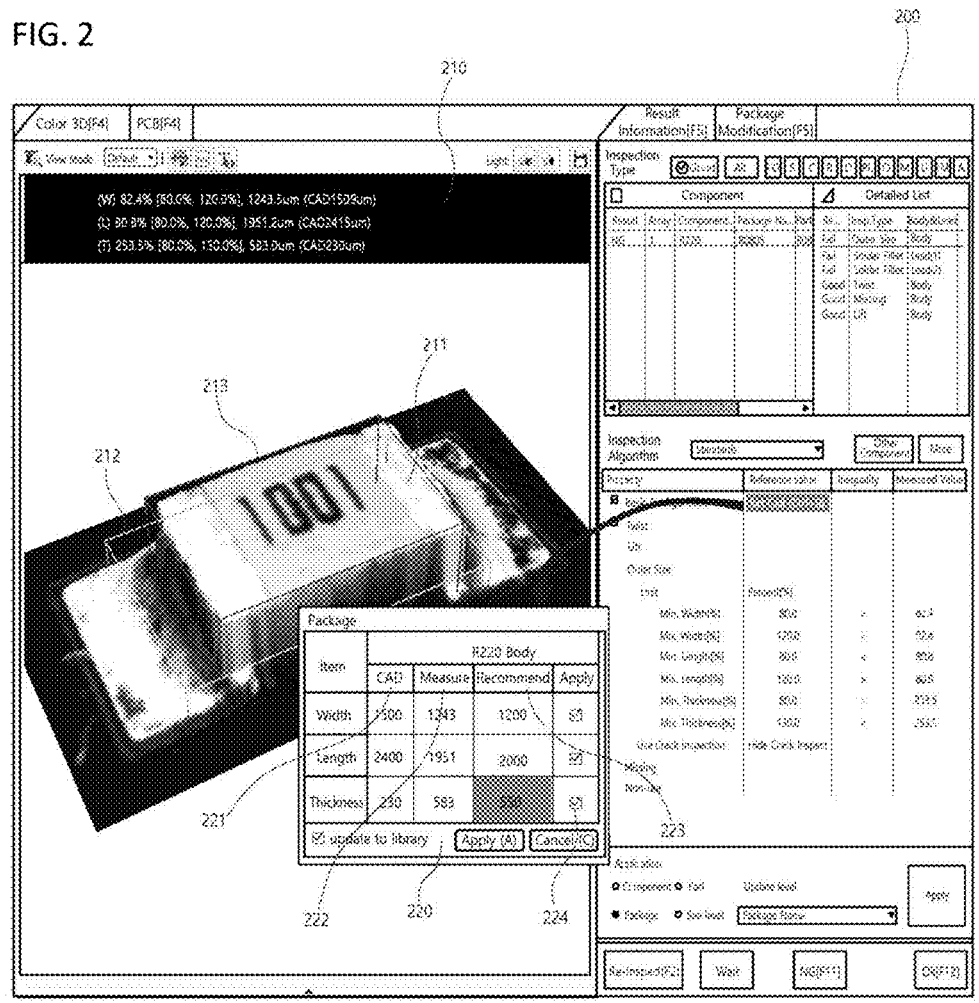
FIG. 2 is a drawing illustrating a graphic user interface for a 3D board inspection apparatus according to an exemplary embodiment of the present invention.

FIG. 1 is a block diagram illustrating a 3D board inspection apparatus for providing a graphic user interface according to an exemplary embodiment of the present invention. FIG. 2 is a drawing illustrating a graphic user interface for a 3D board inspection apparatus according to an exemplary embodiment of the present invention.

Referring to FIG. 1, a 3D board inspection apparatus 100 may include a control section 110 that controls the board inspection apparatus 100 and processes calculation for performing various functions, a stage section 120 that transfers, mounts and fixes a board as a an inspection target, a measuring section 130 that inspects the board mounted on the stage section 120, a memory section 140 that stores a program and data for driving the board inspection apparatus 100, a display section 150 that outputs functional condition, inspection result, etc. of the board inspection apparatus 100, a user interface section 160 that receives user's commands, etc. The program may include a command for forming a graphic user interface, and the graphic user interface may be displayed through the display section 150 by running the program.

The inspection target of the 3D board inspection apparatus 100 may be a component mounted on the board or a lead of the component.

Hereinafter, the 3D board inspection apparatus according to an exemplary embodiment of the present invention will be described principally with regard to constitution of a graphic user interface. Various information and data displayed in the graphic user interface is processed in the 3D board inspection apparatus 100, and thus description for the same will be omitted. In addition, for convenience, an inspection target is assumptively regarded as a component on a board.

Referring to FIG. 2, a graphic user interface 200 for a 3D board inspection apparatus according to an exemplary embodiment of the present invention includes an actual measurement image display area 210 in which a 3D actual measurement image of the inspection target that is formed based on 3D actual measurement data for a component mounted on a board is displayed.

In addition, the graphic user interface 200 includes a dimension information display area 220 in which dimension information of the inspection target is displayed based on the 3D actual measurement data for the component and reference dimension information of the inspection target previously stored in the board inspection apparatus 100. The previously stored reference dimension information of the inspection target corresponds to a reference value to compare with an actual measurement value, and for example, may be obtained from CAD data that is previously stored in the board inspection apparatus 100.

The 3D actual measurement image of the inspection target is displayed rotatable with respect to one of X-axis, Y-axis and Z-axis according to an input value in the actual measurement image display area. Thus, when command concerning rotation with respect to one of X-axis, Y-axis and Z-axis is input through the user interface section 160, the actual measurement image may be rotated and displayed in 3D according to the command.

As shown in FIG. 2, the 3D actual measurement image 211 of the component is enlarged and displayed in the actual measurement image display area 210. A first contour line 212 of the component based on the reference dimension information and a second contour line 213 of the component based on the 3D actual measurement data is displayed with overlapping the 3D actual measurement image of the component in the actual measurement image display area 210.

Each of the first contour line 212 and the second contour line 213 may include at least one of a width line, a length line and a height (corresponding to thickness) line of the inspection target, and may be displayed to include all of the width line, the length line and the height line as shown in FIG. 2. Herein, as shown in FIG. 2, in order for a user to easily distinguish the first contour line 212 and the second contour line 213, the first contour line 212 and the second contour line 213 may be distinctively displayed in a different color from each other.

Since the first contour line 212 and the second contour line 213 are displayed with overlapping the 3D actual measurement image of the component, a user may easily know that a size of the component in the reference dimension information and a size of the component in the actual measurement are different from each other with the unaided eye.

The dimension information display area 220 includes a reference dimension display area 221 for displaying the reference dimension information, an actual measurement dimension display area 222 for displaying the 3D actual measurement data and a recommended dimension display area 223 for displaying recommended dimension information of the inspection target.

The recommended dimension may be calculated with an algorithm predetermined based on the component dimension in the actual measurement data by the control section 120.

The reference dimension information previously stored includes design information such as size information of the component corresponding to coordinates of the component. In order to update the reference dimension information with the recommended dimension information, the dimension display area 200 may include a selection menu 224 to update the reference dimension information by applying the recommended dimension to the reference dimension information.

When a user selects whether to apply through the selection menu 224 in the dimension display area 200 and finally selects "apply (A)", a reference value of the component dimension in the reference dimension information may be changed. For user's convenience, a pointer is configured to move on a screen in the display section 150 by using the user interface section 160, and when a specific input is input at one location of width, length and height of the first contour line 212 or the second contour line 213, update for the reference dimension information of the inspection target that is previously stored replaced with the recommended dimension information corresponding to the one of width, length and height may be configured to be automatically performed.

The input may be an input value such as double click when the user interface section 160 includes a mouse, and may be a screen touch action at a location corresponding to the one of width, length and height when the display section 150 is configured to be a touch screen. These are just examples, and the input is not limited to the above. Herein, when the input is input by a user, "apply" may be automatically selected and displayed in the selection menu 224.

In addition, the graphic user interface 200 for a 3D board inspection apparatus according to an exemplary embodiment of the present invention may include a reference value setup menu 230, and the graphic user interface may be configured so that the dimension information display area 220 is displayed in a pop-up window form when the reference value setup menu 230 is selected.

A user may move a pointer on a screen in the display section 150 by using the user interface 150, and when the pointer is located on the first contour line 212 or the second contour line 213, at least one of width, length and height of the component may be displayed at the location.

In case that a ratio of a dimension of the inspection target in the 3D actual measurement data to a dimension of a component corresponding to the inspection target in the reference dimension information deviates from a predetermined range, it may be necessary for a user to check this in detail since this indicates that difference between the component dimension in the reference dimension information and the component dimension in the actual measurement data exceeds a reference value.

Thus, in order for a user to easily know this, the associated recommended dimension may be displayed to be distinguished from other recommended dimension in the dimension information display area, and only the recommended dimension may be displayed to have a different background color as shown in FIG. 2.

A program including commands for implementing the graphic user interface for a 3D board inspection apparatus according to an exemplary embodiment of the present invention as described above may be recorded in a medium that is readable by a computer. The medium that is readable by a computer may include a program command, a data file, a data structure, etc., singularly or in combination. The program command recorded in the medium may be specifically designed and configured for the present invention or known and usable by a person skilled in the art of a computer software. Examples of the recording medium that is readable by a computer may include magnetic media such as a hard disk, a floppy disk and a magnetic tape, optical media such as a CD-ROM and a DVD, magneto-optical media such as a floptical disk, and hardware devices specifically configured to store and run program commands such as a ROM, a RAM, a flash memory, etc. Examples of the program commands include not only a machine language code such as what is formed by a complier but also a high-level language code that is implementable by using an interpreter, etc.

According to a graphic user interface for a 3D board inspection apparatus in an exemplary embodiment of the present invention, a user may easily check a difference between a dimension in CAD data and a dimension in actual measurement on 3D actual measurement image of a component, and further easily establish a reference value in CAD data based on the dimension in actual measurement, to thereby increase user's convenience of a 3D board inspection apparatus.

It will be apparent to those skilled in the art that various modifications and variation can be made in the present invention by addition, modification, omission, etc. of elements without departing from the spirit or scope of the invention, and it should be understood that the modifications and variation can also be included in the scope of this invention.

The invention claimed is:

1. A device providing a graphic user interface for a three dimensional (3D) board inspection apparatus comprising:
   an actual measurement image display area in which a 3D actual measurement image of an inspection target is displayed based on 3D actual measurement data for the inspection target on a board;
   a dimension information display area in which dimension information of the inspection target is displayed based on the 3D actual measurement data for the inspection target and reference dimension information of the inspection target previously stored in the board inspection apparatus;
   wherein a first contour line of the inspection target based on the reference dimension information and a second contour line of the inspection target based on the 3D actual measurement data are displayed with overlapping the 3D actual measurement image of the inspection target in the actual measurement image display area; and
   wherein the dimension information display area includes a recommended dimension display area for displaying recommended dimension information of the inspection target, and the reference dimension information is updated by applying the recommended dimension information to the reference dimension information according to a specific input.

2. The device providing a graphic user interface for a 3D board inspection apparatus of claim 1, wherein the dimension information display area includes a reference dimension display area for displaying the reference dimension information, and an actual measurement dimension display area for displaying the 3D actual measurement data.

3. The device providing a graphic user interface for a 3D board inspection apparatus of claim 2, wherein a setup menu is displayed in the dimension information display area for updating the reference dimension information with the recommended dimension information of the inspection target that is previously stored.

4. The device providing a graphic user interface for a 3D board inspection apparatus of claim 2, wherein update for the reference dimension information of the inspection target that is previously stored replaced with the recommended dimension information corresponding to the one of width, length and height is automatically performed when a specific input is input at one location of width, length and height of the first contour line or the second contour line.

5. The device providing a graphic user interface for a 3D board inspection apparatus of claim 1, wherein the inspection target is a component mounted on the board or a lead of the component.

6. The device providing a graphic user interface for a 3D board inspection apparatus of claim 1, wherein the first contour line and the second contour line include at least one of a width line, a length line and a height line of the inspection target.

7. The device providing a graphic user interface for a 3D board inspection apparatus of claim 1, wherein the first contour line and the second contour line are displayed in a different color from each other.

8. The device providing a graphic user interface for a 3D board inspection apparatus of claim 1, wherein in case that a ratio of a dimension of the inspection target in the 3D actual measurement data to a dimension of a component corresponding to the inspection target deviates from a predetermined range, a recommended dimension is displayed distinguishable from other recommended dimension in the dimension information display area.

9. The device providing a graphic user interface for a 3D board inspection apparatus of claim 1, wherein the 3D actual measurement image of the inspection target is displayed rotatable with respect to one of X-axis, Y-axis and Z-axis according to an input value in the actual measurement image display area.

10. The device providing a graphic user interface for a 3D board inspection apparatus of claim 1, wherein the graphic user interface for a 3D board inspection apparatus includes a reference value setup menu, and
    when the reference value setup menu is selected, the dimension information display area is displayed in a pop-up window form.

11. The device providing a graphic user interface for a 3D board inspection apparatus of claim 1, wherein when a pointer is located on the first contour line or the second contour line, at least one of width, length and height of the inspection target is displayed at the location.

12. A non transitory computer readable storage medium, wherein the non transitory computer readable storage medium stores commands for executing a graphic user interface that is provided by the device providing a graphic user interface for a 3D board inspection apparatus according to claim 1 is stored in the non transitory computer readable storage medium.

13. A non transitory computer readable storage medium wherein the non transitory computer readable storage medium stores commands for executing a graphic user interface that is provided by the device providing a graphic user interface for a 3D board inspection apparatus according to claim 2 is stored in the non transitory computer readable storage medium.

14. A non transitory computer readable storage medium, wherein the non transitory computer readable storage medium stores commands for executing a graphic user interface that is provided by the device providing a graphic user interface for a 3D board inspection apparatus according to claim 3 is stored in the non transitory computer readable storage medium.

15. A non transitory computer readable storage medium, wherein the non transitory computer readable storage medium stores commands for executing a graphic user interface that is provided by the device providing a graphic user interface for a 3D board inspection apparatus according to claim 4 is stored in the non transitory computer readable storage medium.

16. A non transitory computer readable storage medium, wherein the non transitory computer storage medium stores commands for executing a graphic user interface that is provided by the device providing a graphic user interface for a 3D board inspection apparatus according to claim 6 is stored in the non transitory computer readable storage medium.

17. A non transitory computer readable storage medium, wherein the non transitory computer readable storage medium stores commands for executing a graphic user interface that is provided by the device providing a graphic user interface for a 3D board inspection apparatus according to claim 8 is stored in the non transitory computer readable storage medium.

18. A non transitory computer readable storage medium, wherein the non transitory computer readable storage medium stores commands for executing a graphic user interface that is provided by the device providing a graphic user interface for a 3D board inspection apparatus according to claim 9 is stored in the non transitory computer readable storage medium.

19. A non transitory computer readable storage medium, wherein the non transitory computer readable storage medium stores commands for executing a graphic user interface that is provided by the device providing a graphic user interface for a 3D board inspection apparatus according to claim 10 is stored in the non transitory computer readable storage medium.

20. A non transitory computer readable storage medium, wherein the non transitory computer readable storage medium stores commands for executing a graphic user interface that is provided by the device providing a graphic user interface for a 3D board inspection apparatus according to claim 11 is stored in the non transitory computer readable storage medium.

* * * * *